US011357992B2

United States Patent
Nageri et al.

(10) Patent No.: US 11,357,992 B2
(45) Date of Patent: Jun. 14, 2022

(54) CONNECTOR ASSEMBLY FOR AN ELECTRICAL STIMULATION SYSTEM AND METHODS OF MAKING AND USING

(71) Applicant: Boston Scientific Neuromodulation Corporation, Valencia, CA (US)

(72) Inventors: Ranjan Krishna Mukhari Nageri, Valencia, CA (US); Peter J. Yoo, Burbank, CA (US); Darragh McDermott, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 29 days.

(21) Appl. No.: 16/864,432

(22) Filed: May 1, 2020

(65) Prior Publication Data

US 2020/0346021 A1 Nov. 5, 2020

Related U.S. Application Data

(60) Provisional application No. 62/842,712, filed on May 3, 2019.

(51) Int. Cl.
*A61N 1/05* (2006.01)
*A61N 1/375* (2006.01)

(52) U.S. Cl.
CPC .......... *A61N 1/3752* (2013.01); *A61N 1/0551* (2013.01); *A61N 1/3754* (2013.01)

(58) Field of Classification Search
CPC ...... A61N 1/05; A61N 1/0551; A61N 1/3752; A61N 1/3754
See application file for complete search history.

(56) References Cited

U.S. PATENT DOCUMENTS

| | | | |
|---|---|---|---|
| 3,222,471 | A | 12/1965 | Steinkamp |
| 3,601,747 | A | 8/1971 | Prall et al. |
| 3,718,142 | A | 2/1973 | Mulier |
| 3,757,789 | A | 9/1973 | Shanker |
| 3,771,106 | A | 11/1973 | Matsumoto et al. |
| 3,908,668 | A | 9/1975 | Bolduc |
| 3,951,154 | A | 4/1976 | Hartlaub |
| 3,990,727 | A | 11/1976 | Gallagher |
| 4,003,616 | A | 1/1977 | Springer |

(Continued)

FOREIGN PATENT DOCUMENTS

| | | |
|---|---|---|
| EP | 0580928 A1 | 2/1994 |
| EP | 0650694 B1 | 7/1998 |

(Continued)

*Primary Examiner* — Carl H Layno
*Assistant Examiner* — Anh-Khoa N Dinh
(74) *Attorney, Agent, or Firm* — Branch Partners PLLC; Bruce E. Black

(57) ABSTRACT

A connector and lead (or other elongated body) can produce a tactile sensation that indicates alignment between connector contacts of the connector and the terminals on the lead (or other elongated body). For example, a terminal or retention sleeve of the lead (or other elongated body) may include an indented circumferential groove that interacts with a connector contact or retention contact of the connector to produce the tactile sensation. As another example, one or more terminals or spacers may have a larger diameter than adjacent spacers or terminals to interact with a connector contact to produce the tactile sensation.

19 Claims, 9 Drawing Sheets

(56) References Cited

U.S. PATENT DOCUMENTS

| | | |
|---|---|---|
| 4,112,953 A | 9/1978 | Shanker et al. |
| 4,142,532 A | 3/1979 | Ware |
| 4,180,078 A | 12/1979 | Anderson |
| 4,245,642 A | 1/1981 | Skubitz et al. |
| 4,259,962 A | 4/1981 | Peers-Trevarton |
| 4,310,001 A | 1/1982 | Comben |
| 4,364,625 A | 12/1982 | Baker et al. |
| 4,367,907 A | 1/1983 | Buck |
| 4,411,276 A | 10/1983 | Dickhudt et al. |
| 4,411,277 A | 10/1983 | Dickhudt |
| 4,461,194 A | 7/1984 | Moore |
| 4,466,441 A | 8/1984 | Skubitz et al. |
| 4,516,820 A | 5/1985 | Kuzma |
| RE31,990 E | 9/1985 | Sluetz et al. |
| 4,540,236 A | 9/1985 | Peers-Trevarton |
| 4,602,624 A | 7/1986 | Naples et al. |
| 4,603,696 A | 8/1986 | Cross, Jr. et al. |
| 4,614,395 A | 9/1986 | Peers-Trevarton |
| 4,630,611 A | 12/1986 | King |
| 4,695,116 A | 9/1987 | Bailey et al. |
| 4,695,117 A | 9/1987 | Kysiak |
| 4,712,557 A | 12/1987 | Harris |
| 4,715,380 A | 12/1987 | Harris |
| 4,744,370 A | 5/1988 | Harris |
| 4,784,141 A | 11/1988 | Peers-Trevarton |
| 4,832,032 A | 5/1989 | Schneider |
| 4,840,580 A | 6/1989 | Saell et al. |
| 4,850,359 A | 7/1989 | Putz |
| 4,860,750 A | 8/1989 | Frey et al. |
| 4,867,708 A | 9/1989 | Iizuka |
| 4,869,255 A | 9/1989 | Putz |
| 4,898,173 A | 2/1990 | Daglow et al. |
| 4,899,753 A | 2/1990 | Inoue et al. |
| 4,951,687 A | 8/1990 | Ufford et al. |
| 4,995,389 A | 2/1991 | Harris |
| 5,000,177 A | 3/1991 | Hoffman et al. |
| 5,000,194 A | 3/1991 | van den Honert et al. |
| 5,007,435 A | 4/1991 | Doan et al. |
| 5,007,864 A | 4/1991 | Stutz, Jr. |
| 5,070,605 A | 12/1991 | Daglow et al. |
| 5,082,453 A | 1/1992 | Stutz, Jr. |
| 5,086,773 A | 2/1992 | Ware |
| 5,135,001 A | 8/1992 | Sinofsky et al. |
| 5,193,539 A | 3/1993 | Schulman et al. |
| 5,193,540 A | 3/1993 | Schulman et al. |
| 5,201,865 A | 4/1993 | Kuehn |
| 5,241,957 A | 9/1993 | Camps et al. |
| 5,252,090 A | 10/1993 | Giurtino et al. |
| 5,261,395 A | 11/1993 | Oleen et al. |
| 5,312,439 A | 5/1994 | Loeb |
| 5,324,312 A | 6/1994 | Stokes et al. |
| 5,330,521 A | 7/1994 | Cohen |
| 5,336,246 A | 8/1994 | Dantanarayana |
| 5,348,481 A | 9/1994 | Ortiz |
| 5,354,326 A | 10/1994 | Comben et al. |
| 5,358,514 A | 10/1994 | Schulman et al. |
| 5,368,496 A | 11/1994 | Ranalletta et al. |
| 5,374,279 A | 12/1994 | Duffin, Jr. et al. |
| 5,374,285 A | 12/1994 | Vaiani et al. |
| 5,383,913 A | 1/1995 | Schiff |
| 5,413,595 A | 5/1995 | Stutz, Jr. |
| 5,433,734 A | 7/1995 | Stokes et al. |
| 5,435,731 A | 7/1995 | Kang |
| 5,458,629 A | 10/1995 | Baudino et al. |
| 5,486,202 A | 1/1996 | Bradshaw |
| 5,489,225 A | 2/1996 | Julian |
| 5,509,928 A | 4/1996 | Acken |
| 5,522,874 A | 6/1996 | Gates |
| 5,534,019 A | 7/1996 | Paspa |
| 5,545,188 A | 8/1996 | Bradshaw et al. |
| 5,545,189 A | 8/1996 | Fayram |
| 5,582,180 A | 8/1996 | Manset et al. |
| 5,560,358 A * | 10/1996 | Arnold .................. A61B 5/24 |
| | | 600/373 |
| 5,679,026 A | 10/1997 | Fain et al. |
| 5,683,433 A | 11/1997 | Carson |
| 5,711,316 A | 1/1998 | Elsberry et al. |
| 5,713,922 A | 2/1998 | King |
| 5,720,631 A | 2/1998 | Carson et al. |
| 5,730,628 A | 3/1998 | Hawkins |
| 5,755,743 A | 5/1998 | Volz et al. |
| 5,766,042 A | 6/1998 | Ries et al. |
| 5,782,892 A | 7/1998 | Castle et al. |
| 5,796,044 A | 8/1998 | Cobian et al. |
| 5,800,350 A | 9/1998 | Coppleson et al. |
| 5,800,495 A | 9/1998 | Machek et al. |
| 5,807,144 A | 9/1998 | Sivard |
| 5,837,006 A | 11/1998 | Ocel et al. |
| 5,843,141 A | 12/1998 | Bischoff et al. |
| 5,843,148 A | 12/1998 | Gijsbers et al. |
| 5,906,634 A | 5/1999 | Flynn et al. |
| 5,931,861 A | 8/1999 | Werner et al. |
| 5,938,688 A | 8/1999 | Schiff |
| 5,951,595 A | 9/1999 | Moberg et al. |
| 5,968,082 A | 10/1999 | Heil |
| 5,987,361 A | 11/1999 | Mortimer |
| 5,989,077 A | 11/1999 | Mast et al. |
| 6,006,135 A | 12/1999 | Kast et al. |
| 6,018,684 A | 1/2000 | Bartig et al. |
| 6,038,479 A | 3/2000 | Werner et al. |
| 6,038,481 A | 3/2000 | Werner et al. |
| 6,042,432 A | 3/2000 | Hashazawa et al. |
| 6,051,017 A | 4/2000 | Loeb et al. |
| 6,080,188 A | 6/2000 | Rowley et al. |
| 6,112,120 A | 8/2000 | Correas |
| 6,112,121 A | 8/2000 | Paul et al. |
| 6,125,302 A | 9/2000 | Kuzma |
| 6,134,478 A | 10/2000 | Spehr |
| 6,154,678 A | 11/2000 | Lauro |
| 6,161,047 A | 12/2000 | King et al. |
| 6,162,101 A | 12/2000 | Fischer et al. |
| 6,164,284 A | 12/2000 | Schulman et al. |
| 6,167,311 A | 12/2000 | Rezai |
| 6,167,314 A | 12/2000 | Fischer, Sr. et al. |
| 6,175,710 B1 | 1/2001 | Kamaji et al. |
| 6,181,969 B1 | 1/2001 | Gord |
| 6,185,452 B1 | 2/2001 | Schulman et al. |
| 6,192,278 B1 | 2/2001 | Werner et al. |
| 6,198,969 B1 | 3/2001 | Kuzma |
| 6,208,894 B1 | 3/2001 | Schulman et al. |
| 6,224,450 B1 | 5/2001 | Norton |
| 6,269,266 B1 | 7/2001 | Leysieffer |
| 6,271,094 B1 | 8/2001 | Boyd et al. |
| 6,295,944 B1 | 10/2001 | Lovett |
| 6,319,021 B1 | 11/2001 | Billman |
| 6,321,126 B1 | 11/2001 | Kuzma |
| 6,322,559 B1 | 11/2001 | Daulton et al. |
| 6,343,233 B1 | 1/2002 | Werner et al. |
| 6,364,278 B1 | 4/2002 | Lin et al. |
| 6,370,434 B1 | 4/2002 | Zhang et al. |
| 6,391,985 B1 | 5/2002 | Goode et al. |
| 6,397,108 B1 | 5/2002 | Camps et al. |
| 6,415,168 B1 | 7/2002 | Putz |
| 6,428,336 B1 | 8/2002 | Akerfeldt |
| 6,428,368 B1 | 8/2002 | Hawkins et al. |
| 6,430,442 B1 | 8/2002 | Peters et al. |
| 6,466,824 B1 | 10/2002 | Struble |
| 6,473,654 B1 | 10/2002 | Chinn |
| 6,498,952 B2 | 12/2002 | Imani et al. |
| 6,510,347 B2 | 1/2003 | Borkan |
| 6,516,227 B1 | 2/2003 | Meadows et al. |
| 6,556,873 B1 | 4/2003 | Smits |
| 6,564,078 B1 | 5/2003 | Marino et al. |
| 6,604,283 B1 | 8/2003 | Kuzma |
| 6,605,094 B1 | 8/2003 | Mann et al. |
| 6,609,029 B1 | 8/2003 | Mann et al. |
| 6,609,032 B1 | 8/2003 | Woods et al. |
| 6,654,641 B1 | 11/2003 | Froberg |
| 6,662,035 B2 | 12/2003 | Sochor |
| 6,663,570 B2 | 12/2003 | Mott |
| 6,671,534 B2 | 12/2003 | Putz |
| 6,671,553 B1 | 12/2003 | Helland et al. |
| 6,678,564 B2 | 1/2004 | Ketterl et al. |
| 6,705,900 B2 | 3/2004 | Sommer et al. |

(56) References Cited

U.S. PATENT DOCUMENTS

| | | |
|---|---|---|
| 6,725,096 B2 | 4/2004 | Chinn et al. |
| 6,741,892 B1 | 5/2004 | Meadows et al. |
| 6,757,039 B2 | 6/2004 | Ma |
| 6,757,970 B1 | 7/2004 | Kuzma et al. |
| 6,799,991 B2 | 10/2004 | Williams et al. |
| 6,805,675 B1 | 10/2004 | Gardeski et al. |
| 6,854,994 B2 | 2/2005 | Stein et al. |
| 6,878,013 B1 | 4/2005 | Behan |
| 6,895,276 B2 | 5/2005 | Kast et al. |
| 6,895,280 B2 | 5/2005 | Meadows et al. |
| 6,913,478 B2 | 7/2005 | Lamirey |
| 6,921,295 B2 | 7/2005 | Sommer et al. |
| 6,968,235 B2 | 11/2005 | Belden et al. |
| 6,980,863 B2 | 12/2005 | van Venrooij et al. |
| 7,027,852 B2 | 4/2006 | Helland |
| 7,047,084 B2 | 5/2006 | Erickson et al. |
| 7,058,452 B2 | 6/2006 | Dahberg |
| 7,069,081 B2 | 6/2006 | Biggs et al. |
| 7,083,474 B1 | 8/2006 | Fleck et al. |
| 7,108,549 B2 | 9/2006 | Lyu et al. |
| 7,110,827 B2 | 9/2006 | Sage et al. |
| 7,128,600 B2 | 10/2006 | Osypka |
| 7,155,283 B2 | 12/2006 | Ries et al. |
| 7,164,951 B2 | 1/2007 | Ries et al. |
| 7,168,165 B2 | 1/2007 | Calzada et al. |
| 7,191,009 B2 | 3/2007 | Laske et al. |
| 7,195,523 B2 | 3/2007 | Naviaux |
| 7,203,548 B2 | 4/2007 | Whitehurst et al. |
| 7,225,034 B2 | 5/2007 | Ries et al. |
| 7,231,253 B2 | 6/2007 | Tidemand et al. |
| 7,241,180 B1 | 7/2007 | Rentas |
| 7,242,987 B2 | 7/2007 | Holleman et al. |
| 7,244,150 B1 | 7/2007 | Brase et al. |
| 7,270,568 B2 | 9/2007 | Osypka |
| 7,283,878 B2 | 10/2007 | Brostrom et al. |
| 7,286,882 B2 | 10/2007 | Cole |
| 7,287,995 B2 | 10/2007 | Stein et al. |
| 7,292,890 B2 | 11/2007 | Whitehurst et al. |
| 7,396,335 B2 | 7/2008 | Gardeski et al. |
| 7,402,083 B2 | 7/2008 | Kast et al. |
| 7,422,487 B2 | 9/2008 | Osypka |
| 7,430,958 B2 | 10/2008 | Wong |
| 7,437,193 B2 | 10/2008 | Parramon et al. |
| 7,450,997 B1 | 11/2008 | Pianca et al. |
| 7,489,971 B1 * | 2/2009 | Franz ............... A61N 1/0551 607/116 |
| 7,512,446 B2 | 3/2009 | Honeck |
| 7,516,447 B2 | 3/2009 | Drew |
| 7,526,339 B2 | 4/2009 | Lahti et al. |
| 7,539,542 B1 | 5/2009 | Malinowski |
| 7,548,788 B2 | 6/2009 | Chinn et al. |
| 7,554,493 B1 | 6/2009 | Rahman |
| 7,583,999 B2 | 9/2009 | Bedenbaugh |
| 7,585,190 B2 | 9/2009 | Osypka |
| 7,590,451 B2 | 9/2009 | Tronnes et al. |
| 7,650,184 B2 | 1/2010 | Walter |
| 7,668,601 B2 | 2/2010 | Hegland et al. |
| 7,672,734 B2 | 3/2010 | Anderson et al. |
| 7,736,191 B1 | 6/2010 | Sochor |
| 7,758,384 B2 | 7/2010 | Alexander et al. |
| 7,761,165 B1 | 7/2010 | He et al. |
| 7,761,985 B2 | 7/2010 | Hegland et al. |
| 7,783,359 B2 | 8/2010 | Meadows |
| 7,792,590 B1 | 9/2010 | Pianca et al. |
| 7,798,864 B2 | 9/2010 | Barker et al. |
| 7,803,021 B1 | 9/2010 | Brase |
| 7,809,446 B2 | 10/2010 | Meadows |
| 7,822,477 B2 | 10/2010 | Rey et al. |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,949,395 B2 | 5/2011 | Kuzma |
| 7,974,705 B2 | 7/2011 | Zdeblick et al. |
| 7,974,706 B2 | 7/2011 | Moffitt et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,046,073 B1 | 10/2011 | Pianca |
| 8,046,074 B2 | 10/2011 | Barker |
| 8,078,280 B2 | 12/2011 | Sage |
| 8,099,177 B2 | 1/2012 | Dahlberg |
| 8,100,726 B2 | 1/2012 | Harlan et al. |
| 8,140,163 B1 | 3/2012 | Daglow et al. |
| 8,162,684 B1 | 4/2012 | Sochor |
| 8,167,660 B2 | 5/2012 | Dilmaghanian et al. |
| 8,175,710 B2 | 5/2012 | He |
| 8,190,259 B1 | 5/2012 | Smith et al. |
| 8,206,180 B1 | 6/2012 | Kast et al. |
| 8,224,450 B2 | 7/2012 | Brase |
| 8,225,504 B2 | 7/2012 | Dye et al. |
| 8,239,042 B2 | 8/2012 | Chinn et al. |
| 8,267,708 B1 | 9/2012 | Sochor |
| 8,271,094 B1 | 9/2012 | Moffitt et al. |
| 8,295,944 B2 | 10/2012 | Howard et al. |
| 8,301,255 B2 | 10/2012 | Barker |
| 8,321,025 B2 | 11/2012 | Bedenbaugh |
| 8,342,887 B2 | 1/2013 | Gleason et al. |
| 8,359,107 B2 | 1/2013 | Pianca et al. |
| 8,364,278 B2 | 1/2013 | Pianca et al. |
| 8,391,985 B2 | 3/2013 | McDonald |
| 8,412,330 B2 | 4/2013 | Kast et al. |
| 8,473,061 B2 | 6/2013 | Moffitt et al. |
| 8,527,054 B2 | 9/2013 | North |
| 8,543,222 B1 | 9/2013 | Sochor |
| 8,548,582 B2 | 10/2013 | McDonald et al. |
| 8,571,665 B2 | 10/2013 | Moffitt et al. |
| 8,583,237 B2 | 11/2013 | Bedenbaugh |
| 8,600,507 B2 | 12/2013 | Brase et al. |
| 8,682,439 B2 | 3/2014 | DeRohan et al. |
| 8,688,235 B1 | 4/2014 | Pianca et al. |
| 8,751,002 B2 | 6/2014 | Kast et al. |
| 8,761,887 B2 | 6/2014 | Schramm et al. |
| 8,784,143 B2 | 7/2014 | Edgell et al. |
| 8,792,993 B2 | 7/2014 | Pianca et al. |
| 8,831,742 B2 | 9/2014 | Pianca et al. |
| 8,849,396 B2 | 9/2014 | DeRohan et al. |
| 8,849,415 B2 | 9/2014 | Bedenbaugh |
| 8,897,876 B2 | 11/2014 | Sundaramurthy et al. |
| 8,897,891 B2 | 11/2014 | Romero |
| 8,968,331 B1 | 3/2015 | Sochor |
| 9,101,775 B2 | 8/2015 | Barker |
| 9,149,630 B2 | 10/2015 | Howard et al. |
| 9,162,048 B2 | 10/2015 | Romero et al. |
| 9,234,591 B2 | 1/2016 | Dilmaghanian et al. |
| 9,270,070 B2 | 2/2016 | Pianca |
| 9,289,596 B2 | 3/2016 | Leven |
| 9,352,147 B2 | 5/2016 | Nguyen-stella et al. |
| 9,381,348 B2 | 7/2016 | Romero et al. |
| 9,403,022 B2 | 8/2016 | Ries et al. |
| 9,409,032 B2 | 8/2016 | Brase et al. |
| 9,440,066 B2 | 9/2016 | Black |
| 9,498,618 B2 | 11/2016 | Stetson et al. |
| 9,498,620 B2 | 11/2016 | Romero et al. |
| 9,504,839 B2 | 11/2016 | Leven |
| 9,555,242 B2 | 1/2017 | Hartley et al. |
| 9,564,749 B2 | 2/2017 | Boutaud |
| 9,604,068 B2 | 3/2017 | Malinowski |
| 9,656,093 B2 | 5/2017 | Villarta et al. |
| 9,770,598 B2 | 9/2017 | Malinowski et al. |
| 9,855,413 B2 | 1/2018 | Vadlamudi et al. |
| 2001/0023368 A1 | 9/2001 | Black et al. |
| 2002/0143376 A1 | 10/2002 | Chinn et al. |
| 2002/0156513 A1 | 10/2002 | Borkan |
| 2002/0183817 A1 | 12/2002 | Van Venrooij et al. |
| 2003/0163171 A1 | 8/2003 | Kast et al. |
| 2004/0064164 A1 | 4/2004 | Ries et al. |
| 2004/0176816 A1 | 9/2004 | Singhal et al. |
| 2004/0230268 A1 | 11/2004 | Huff et al. |
| 2004/0260373 A1 | 12/2004 | Ries et al. |
| 2004/0267332 A1 | 12/2004 | Kast et al. |

(56) References Cited

U.S. PATENT DOCUMENTS

| | | |
|---|---|---|
| 2005/0015130 A1 | 1/2005 | Gill |
| 2005/0027326 A1 | 2/2005 | Ries et al. |
| 2005/0027327 A1 | 2/2005 | Ries et al. |
| 2005/0038489 A1 | 2/2005 | Grill |
| 2005/0043770 A1 | 2/2005 | Hine et al. |
| 2005/0043771 A1 | 2/2005 | Sommer et al. |
| 2005/0137665 A1 | 6/2005 | Cole |
| 2005/0171587 A1 | 8/2005 | Daglow et al. |
| 2005/0186829 A1 | 8/2005 | Balsells |
| 2005/0272280 A1 | 12/2005 | Osypka |
| 2006/0015163 A1 | 1/2006 | Brown |
| 2006/0025841 A1 | 2/2006 | McIntyre |
| 2006/0030918 A1 | 2/2006 | Chinn |
| 2006/0167522 A1 | 7/2006 | Malinowski |
| 2006/0224208 A1 | 10/2006 | Naviaux |
| 2006/0247697 A1 | 11/2006 | Sharma et al. |
| 2006/0247749 A1 | 11/2006 | Colvin |
| 2006/0259106 A1 | 11/2006 | Arnholdt et al. |
| 2007/0042648 A1 | 2/2007 | Balsells |
| 2007/0142889 A1 | 6/2007 | Whitehurst et al. |
| 2007/0150036 A1 | 6/2007 | Anderson |
| 2007/0161294 A1 | 7/2007 | Brase et al. |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0215125 A1 | 9/2008 | Farah et al. |
| 2008/0255647 A1 | 10/2008 | Jensen et al. |
| 2008/0274651 A1 | 11/2008 | Boyd et al. |
| 2009/0012591 A1* | 1/2009 | Barker ............... A61N 1/05 607/116 |
| 2009/0054941 A1 | 2/2009 | Eggen et al. |
| 2009/0187222 A1 | 7/2009 | Barker |
| 2009/0204192 A1 | 8/2009 | Carlton et al. |
| 2009/0233491 A1 | 9/2009 | Barker et al. |
| 2009/0264943 A1 | 10/2009 | Barker |
| 2009/0276021 A1 | 11/2009 | Meadows et al. |
| 2009/0287191 A1 | 11/2009 | Ferren et al. |
| 2010/0029127 A1 | 2/2010 | Sjostedt |
| 2010/0030298 A1 | 2/2010 | Martens et al. |
| 2010/0036468 A1 | 2/2010 | Decre et al. |
| 2010/0057176 A1 | 3/2010 | Barker |
| 2010/0070012 A1 | 3/2010 | Chinn et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0004267 A1 | 1/2011 | Meadows |
| 2011/0005069 A1 | 1/2011 | Pianca |
| 2011/0022100 A1 | 1/2011 | Brase et al. |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0184480 A1 | 7/2011 | Kast et al. |
| 2011/0238129 A1 | 9/2011 | Moffitt et al. |
| 2011/0245903 A1 | 10/2011 | Schulte et al. |
| 2011/0270330 A1 | 11/2011 | Janzig et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0053646 A1 | 3/2012 | Brase et al. |
| 2012/0071937 A1 | 3/2012 | Sundaramurthy et al. |
| 2012/0071949 A1 | 3/2012 | Pianca et al. |
| 2012/0165911 A1 | 6/2012 | Pianca |
| 2012/0185019 A1 | 7/2012 | Schramm et al. |
| 2012/0197375 A1 | 8/2012 | Pianca et al. |
| 2012/0203302 A1 | 8/2012 | Moffit et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0253443 A1 | 10/2012 | Dilmaghanian et al. |
| 2012/0259386 A1 | 10/2012 | DeRohan et al. |
| 2012/0316615 A1 | 12/2012 | DiGiore et al. |
| 2013/0035732 A1 | 2/2013 | Miltich et al. |
| 2013/0053864 A1 | 2/2013 | Geroy et al. |
| 2013/0098678 A1 | 4/2013 | Barker |
| 2013/0105071 A1 | 5/2013 | DiGiore et al. |
| 2013/0109254 A1 | 5/2013 | Klardie et al. |
| 2013/0116754 A1 | 5/2013 | Sharma et al. |
| 2013/0149031 A1 | 6/2013 | Changsrivong et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0218154 A1 | 8/2013 | Carbunaru |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0148885 A1 | 5/2014 | DeRohan et al. |
| 2014/0180375 A1 | 6/2014 | Pianca et al. |
| 2014/0214130 A1 | 7/2014 | Lopez et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0025609 A1 | 1/2015 | Govea |
| 2015/0045864 A1 | 2/2015 | Howard |
| 2015/0051681 A1 | 2/2015 | Hershey |
| 2015/0066120 A1 | 3/2015 | Govea |
| 2015/0119965 A1 | 4/2015 | Govea |
| 2015/0151113 A1 | 6/2015 | Govea et al. |
| 2015/0209575 A1 | 7/2015 | Black |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1* | 5/2016 | Malinowski ............ A61N 1/05 607/116 |
| 2016/0129265 A1 | 5/2016 | Malinowski |
| 2016/0158558 A1 | 6/2016 | Shanahan et al. |
| 2016/0206891 A1 | 7/2016 | Howard et al. |
| 2016/0228692 A1 | 8/2016 | Steinke et al. |
| 2016/0263384 A1 | 9/2016 | Stevenson et al. |
| 2016/0296745 A1 | 10/2016 | Govea et al. |
| 2016/0375238 A1 | 12/2016 | Leven et al. |
| 2017/0014635 A1 | 1/2017 | Villarta et al. |
| 2017/0072187 A1 | 3/2017 | Howard et al. |
| 2017/0143978 A1 | 5/2017 | Barker |
| 2017/0203104 A1 | 7/2017 | Nageri et al. |
| 2017/0361108 A1 | 12/2017 | Leven |
| 2018/0008832 A1 | 1/2018 | Leven |
| 2018/0028820 A1 | 2/2018 | Nageri |
| 2018/0093098 A1 | 4/2018 | Nageri et al. |
| 2018/0126175 A1 | 5/2018 | Seitz et al. |
| 2018/0214687 A1 | 8/2018 | Nageri et al. |
| 2018/0243570 A1 | 8/2018 | Malinowski et al. |
| 2018/0289968 A1 | 10/2018 | Lopez |
| 2018/0369596 A1 | 12/2018 | Funderburk |

(56) References Cited

U.S. PATENT DOCUMENTS

| | | |
|---|---|---|
| 2019/0030345 A1 | 1/2019 | Funderburk |
| 2019/0083793 A1 | 3/2019 | Nageri |
| 2019/0083794 A1 | 3/2019 | Nageri |
| 2019/0103696 A1 | 4/2019 | Conger |
| 2019/0143125 A1 | 5/2019 | Van Funderburk et al. |
| 2019/0192861 A1 | 6/2019 | Lopez et al. |
| 2019/0217103 A1 | 7/2019 | Lopez |
| 2019/0290924 A1 | 9/2019 | Van Funderburk |

FOREIGN PATENT DOCUMENTS

| | | |
|---|---|---|
| EP | 0832667 B1 | 2/2004 |
| EP | 1181947 B1 | 1/2006 |
| EP | 1625875 | 2/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

\* cited by examiner

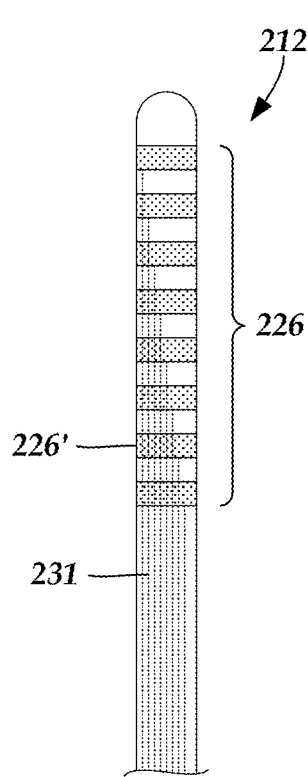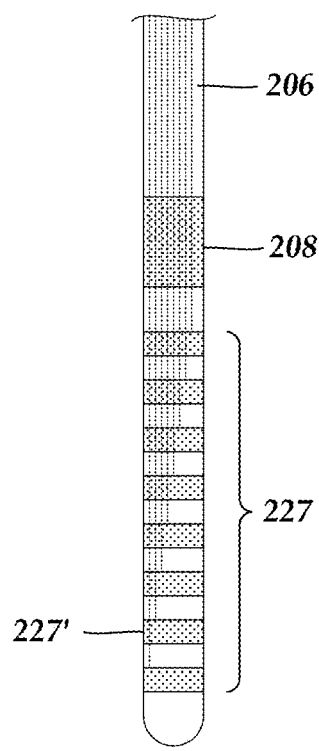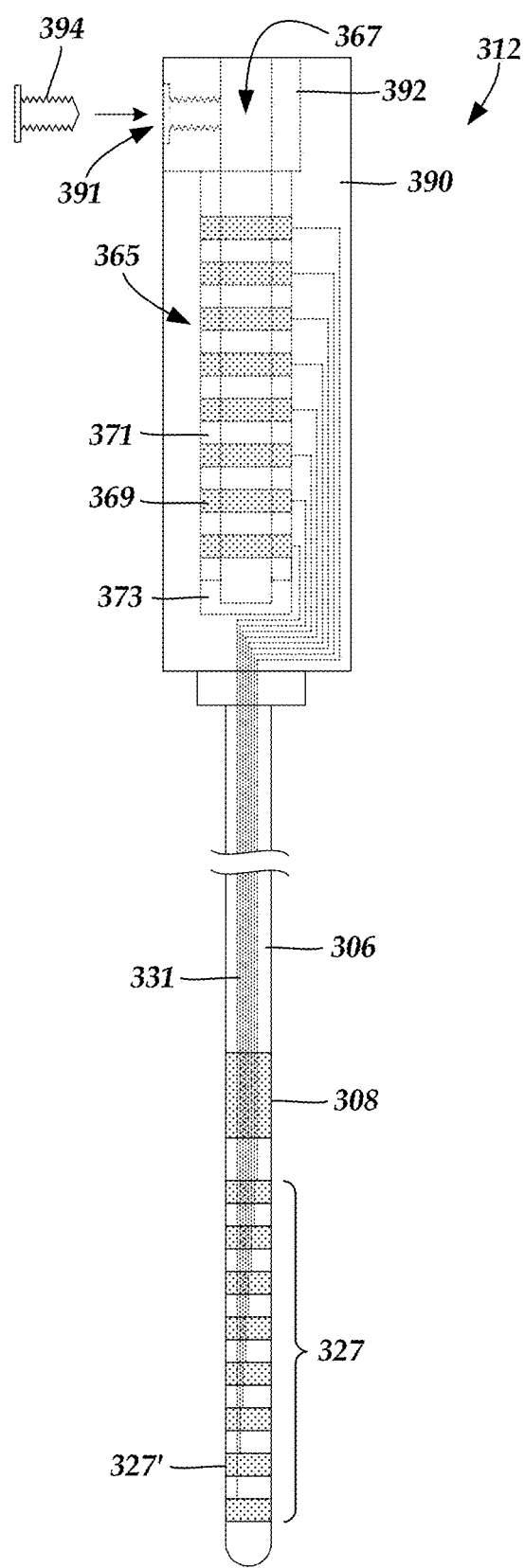
Fig. 2
Fig. 3

CONNECTOR ASSEMBLY FOR AN ELECTRICAL STIMULATION SYSTEM AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/842,712, filed May 3, 2019, which is incorporated herein by reference.

FIELD

The present disclosure is directed to the area of implantable electrical stimulation systems and methods of making and using the systems. The present disclosure is also directed to a connector assembly for an electrical stimulation system, as well the system and methods for making and using the connector.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Deep brain stimulation can be used to treat a variety of diseases and disorders.

Stimulators have been developed to provide therapy for a variety of treatments. A stimulator can include a control module (with a pulse generator) and one or more stimulator electrodes. The one or more stimulator electrodes can be disposed along one or more leads, or along the control module, or both. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a stimulation system that includes a connector defining a connector port and a connector lumen extending from the port, the connector including a plurality of connector contacts disposed along the connector lumen; and an implantable lead including a lead body having a proximal end section and a distal end section, electrodes arranged along the distal end section of the lead body, terminals arranged along the proximal end section of the lead body, wherein at least one of the terminals includes an indented circumferential groove, and conductors extending within the lead body and electrically coupling the electrodes to the terminals. The connector lumen is configured for user insertion of the proximal end section of the lead body of the lead and, when fully inserted, align the connector contacts of the connector with the terminals of the lead. The connector and lead are configured so that alignment of the at least one of the terminals with the indented circumferential groove with a one of the connector contacts produces a tactile sensation for the user inserting the proximal end section of the lead body into the connector lumen.

In at least some aspects, a distalmost terminal of the plurality of terminals includes the indented circumferential groove. In at least some aspects, a plurality of the terminals each includes the indented circumferential groove.

In at least some aspects, the indented circumferential groove extends around an entire circumference of the at least one terminal. In at least some aspects, the indented circumferential groove does not extend around an entire circumference of the at least one terminal, but does extend around at least 20% of the circumference of the at least one terminal.

Another aspect is a stimulation system that includes a connector defining a connector port and a connector lumen extending from the port, the connector including a plurality of connector contacts disposed along the connector lumen; and an implantable lead including a lead body having a proximal end section and a distal end section and including spacers, electrodes arranged along the distal end section of the lead body, terminals arranged along the proximal end section of the lead body, wherein each of the spacers separates adjacent terminals, and conductors extending within the lead body and electrically coupling the electrodes to the terminals. Either i) at least one of the spacers has a larger outer diameter than an outer diameter of the terminals or ii) at least one of the terminals has a larger outer diameter than an outer diameter of the spacers. The connector lumen is configured for user insertion of the proximal end section of the lead body of the lead and, when fully inserted, align the connector contacts of the connector with the terminals of the lead. The connector and lead are configured so that, as the at least one of the spacers or the at least one of the electrodes with the larger outer diameter is inserted past each of the connector contacts, a tactile sensation for the user inserting the proximal end section of the lead body into the connector lumen is produced.

In at least some aspects, the at least one of the spacers has the larger outer diameter. In at least some aspects, a spacer proximal to, and adjacent, a distalmost terminal of the plurality of terminals has the larger outer diameter. In at least some aspects, a plurality of the spacers have the larger outer diameter.

In at least some aspects, the at least one of the terminals has the larger outer diameter. In at least some aspects, a penultimate terminal, with respect to the proximal end of the lead, of the plurality of terminals has the larger outer diameter. In at least some aspects, a plurality of the terminals have the larger outer diameter.

Yet another aspect is a stimulation system that includes a connector defining a connector port and a connector lumen extending from the port, the connector including connector contacts disposed along the connector lumen and a retention contact disposed along the connector lumen or distal to the connector lumen. The stimulation system also includes an implantable lead including a lead body having a proximal end section and a distal end section, electrodes arranged along the distal end section of the lead body, terminals arranged along the proximal end section of the lead body, a retention sleeve disposed along the proximal end section of the lead body and distal to the terminals, wherein the retention sleeve includes an indented circumferential groove, and conductors extending within the lead body and electrically coupling the electrodes to the terminals. The connector lumen is configured for user insertion of the proximal end section of the lead body of the lead and, when fully inserted, align the connector contacts of the connector with the terminals of the lead. The connector and lead are configured so that alignment of the indented circumferential groove of the retention sleeve with the retention contact produces a tactile sensation for the user inserting the proximal end section of the lead body into the connector lumen.

In at least some aspects, the indented circumferential groove extends around an entire circumference of the retention sleeve. In at least some aspects, the indented circumferential groove does not extend around an entire circumference of the retention sleeve, but does extend around at least 20% of the circumference of the retention sleeve.

In at least some aspects, the connector includes a retention block with a contact housing within which the retention contact is disposed. In at least some aspects, the retention block further defines a retention lumen for receiving a retaining element for pressing against the retention sleeve of the lead for retention of the lead within the connector. In at least some aspects, the retention block does not include a retention lumen and the retention contact is configured for exerting a force to retain the lead within the connector. In at least some aspects, the contact housing and the retention contact are adhesively attached to a remainder of the connector. In at least some aspects, the retention contact is configured to only be released from the circumferential groove by use of a tool inserted into the retention block.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2 is a schematic side view of one embodiment of an electrical stimulation lead;

FIG. 3 is a schematic side view of one embodiment of a lead extension suitable for coupling with the electrical stimulation lead of FIG. 2;

DETAILED DESCRIPTION

The present disclosure is directed to the area of implantable electrical stimulation systems and methods of making and using the systems. The present disclosure is also directed to a connector assembly for an electrical stimulation system, as well the system and methods for making and using the connector.

Suitable implantable electrical stimulation systems include, but are not limited to, a least one lead with one or more electrodes disposed on a distal portion of the lead and one or more terminals disposed on one or more proximal portions of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734;7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated herein by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, or peripheral nerve stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
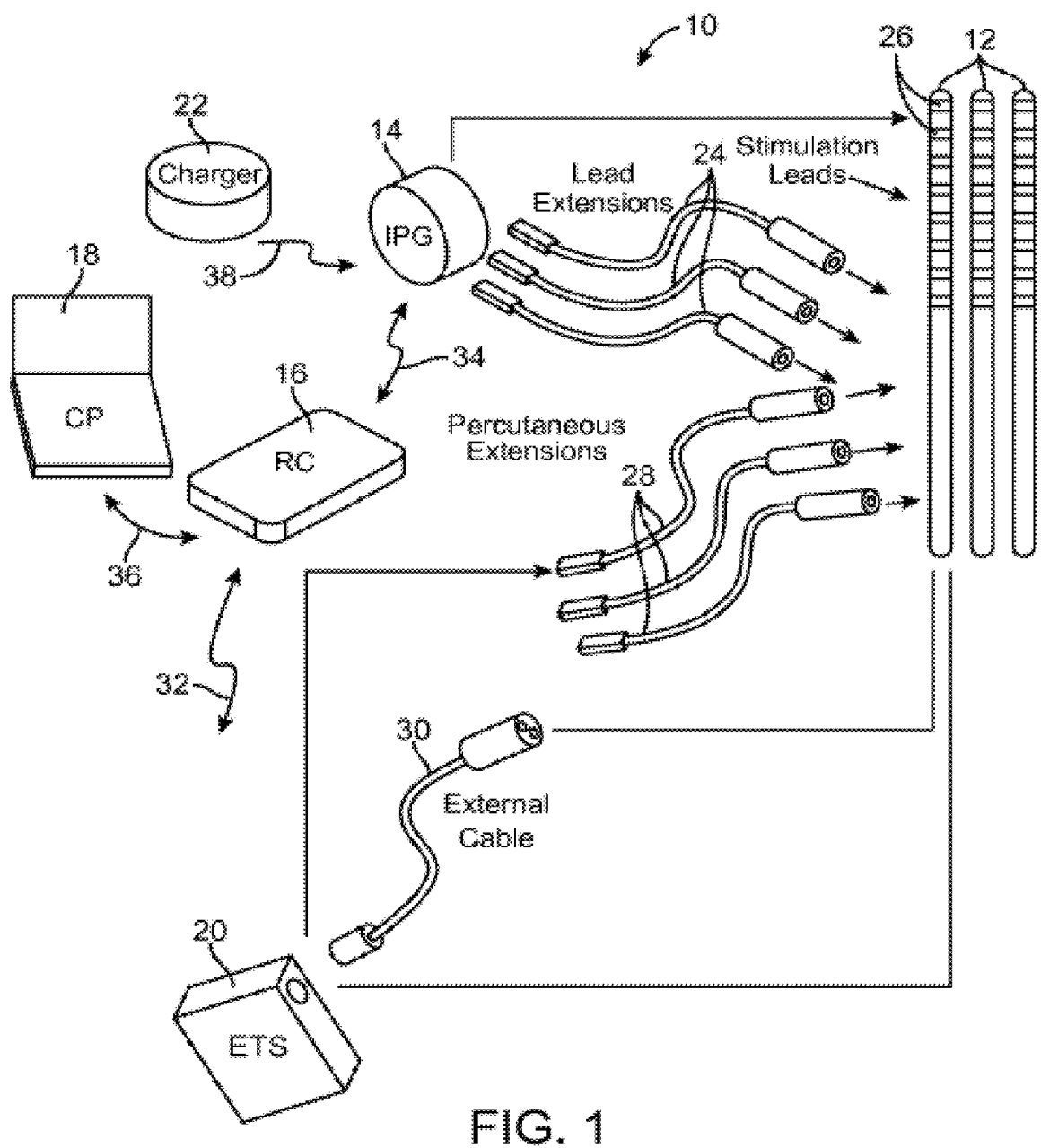
FIG. 1 is a schematic view of one embodiment of an electrical stimulation system.

Turning to FIG. 1, one embodiment of an electrical stimulation system 10 includes one or more stimulation leads 12 and an implantable pulse generator (IPG) 14.

The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity or at any other suitable site. The implantable pulse generator can have multiple stimulation channels which may be independently programmable to control the magnitude of the current stimulus from each channel. In some embodiments, the implantable pulse generator can have any suitable number of stimulation channels including, but not limited to, 4, 6, 8, 12, 16, 32, or more stimulation channels. The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated herein by reference.

Turning to FIG. 2, one or more leads are configured for coupling with a control module. The term "control module" is used herein to describe a pulse generator (e.g., the IPG 14 or the ETS 20 of FIG. 1). Stimulation signals generated by the control module are emitted by electrodes of the lead(s) to stimulate patient tissue. The electrodes of the lead(s) are electrically coupled to terminals of the lead(s) that, in turn, are electrically coupleable with the control module. In some embodiments, the lead(s) couple(s) directly with the control module. In other embodiments, one or more intermediary devices (e.g., a lead extension, an adaptor, a splitter, or the like) are disposed between the lead(s) and the control module.

Percutaneous leads are described herein for clarity of illustration. It will be understood that paddle leads and cuff leads can be used in lieu of, or in addition to, percutaneous leads. Some of the leads described herein include 8 electrodes. It will be understood that the leads could include any suitable number of electrodes. The leads described herein exclusively include ring electrodes. It will be understood that the leads can include a distal-tip electrode, or one or more segmented electrodes in lieu of, or in addition to one or more ring electrodes. Additionally, the term "elongated member" used herein includes leads (e.g., percutaneous, paddle, cuff, or the like), as well as intermediary devices (e.g., lead extensions, adaptors, splitters, or the like).

FIG. 2 shows, in schematic side view, one embodiment of a lead 212 suitable for implanting into a patient and providing electrical stimulation. In some embodiments, the lead 212 is coupled directly to a control module. In other embodiments, the lead 212 is coupled to the control module via one or more intermediary devices. In the illustrated embodiment, an array of electrodes 226, which includes electrode 226', is disposed along a distal portion of a lead body 206 lead and an array of lead terminals 227, which includes lead terminal 227', is disposed along a proximal portion of the lead body. Lead conductors, such as lead conductor 231, extend along a longitudinal length of the lead and electrically couple the array of electrodes 226 to the array lead terminals 227.

Conductors can extend along the longitudinal length of the lead within one or more lumens defined in the lead. In other instances, the conductors may extend along the lead within the lead body itself. The lead 212 includes a retention sleeve 208 disposed along the proximal portion of the body to facilitate coupling of the proximal portion of the lead to a connector. The connector may be disposed in a control module. Alternatively, the retention sleeve 208 can be used to facilitate coupling of the proximal portion of the lead to a connector of an intermediary device, such as a lead extension which, in turn, is coupled to a connector of a control module.

FIG. 3 shows, in schematic side view, one embodiment of a lead extension 312 suitable for implanting into a patient and coupling a lead, such as the lead 212, to a control module. The lead extension 312 includes a lead-extension body 306 having a distal portion and a proximal portion. A lead-extension connector 390 is disposed along the distal portion of the lead-extension body 306 and an array of lead-extension terminals 327, such as lead-extension terminal 327', are disposed along the proximal portion of the lead-extension body 306.

The lead-extension connector 390 contains a lead-extension connector stack 365 that defines a connector lumen 367 configured to receive the proximal portion of an elongated member (e.g., lead 212). The lead-extension connector stack 365 includes lead-extension connector contacts, such as lead-extension connector contact 369, arranged along the connector lumen 367 and configured to electrically couple with terminals of the elongated member (e.g., lead 212) when the proximal portion of the elongated member is received by the lead-extension connector 390. The connector contacts can be electrically isolated from one another by electrically-nonconductive spacers, such as spacer 371. The connector stack may also include an end stop 373 to facilitate alignment of the elongated-member terminals with the lead-extension connector contacts.

The lead-extension connector 390 further includes a retention assembly for facilitating retention of the proximal portion of the elongated member (e.g., lead 212) when the proximal portion of the elongated member is received by the lead-extension connector 390. In the illustrated embodiment, the retention assembly includes a lead-extension retention block 392. The lead-extension retention block 392 is positioned to align with the retention sleeve (208 in FIG. 2) of the elongated member when the elongated member is received by the lead-extension connector 390. In the illustrated embodiment, the retention assembly further includes retention lumen 391 and a retaining member 394 (e.g., a set screw, a pin, or the like) for insertion into the retention lumen and pressing the retention sleeve of the inserted elongated member against the retention block to retain inserted elongated member within the lead-extension connector 390.

Lead-extension conductors, such as lead-extension conductor 331, extend along a longitudinal length of the lead extension and electrically couple the lead-extension connector contacts to the array of lead-extension terminals 327. The lead-extension conductors can extend along the longitudinal length of the lead-extension body within one or more lumens defined in the lead extension. In other instances, the lead-extension conductors may extend along the lead extension within the lead-extension body itself. The lead extension 312 includes a retention sleeve 308 disposed along the proximal portion of the lead-extension body to facilitate coupling of the proximal portion of the lead extension to a connector, such as a control-module connector, another lead-extension connector, or the like.

Figure 4:
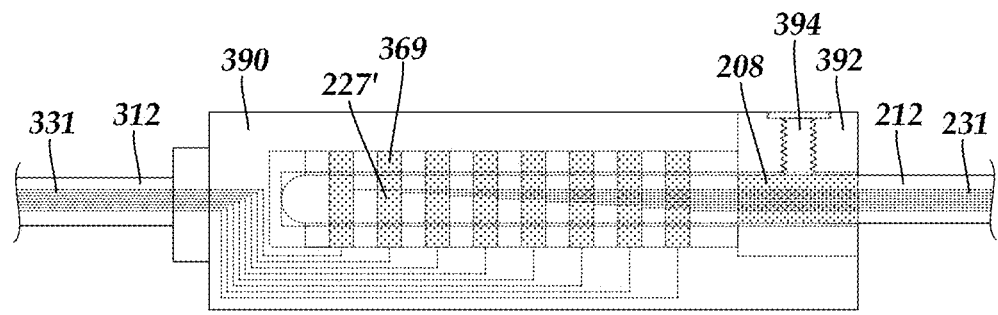
FIG. 4 is a schematic side view of one embodiment of the lead of FIG. 2 coupled to the lead extension of FIG. 3.

FIG. 4 shows, in schematic side view, one embodiment of the lead 212 received by the lead-extension connector 390. In the illustrated embodiment, the lead terminals 227, such as lead terminal 227', are aligned with the lead-extension connector contacts, such as lead-extension connector contact 369. Accordingly, the lead conductors 231 are electrically coupled with the lead-extension conductors 331. Additionally, in the illustrated embodiment the lead retention sleeve 208 is aligned with the lead-extension retention block 392 and the retaining member 394 is pressing the lead retention sleeve 208 against the lead-extension retention block to retain the lead 212 within the lead-extension connector 390.

Figure 5:
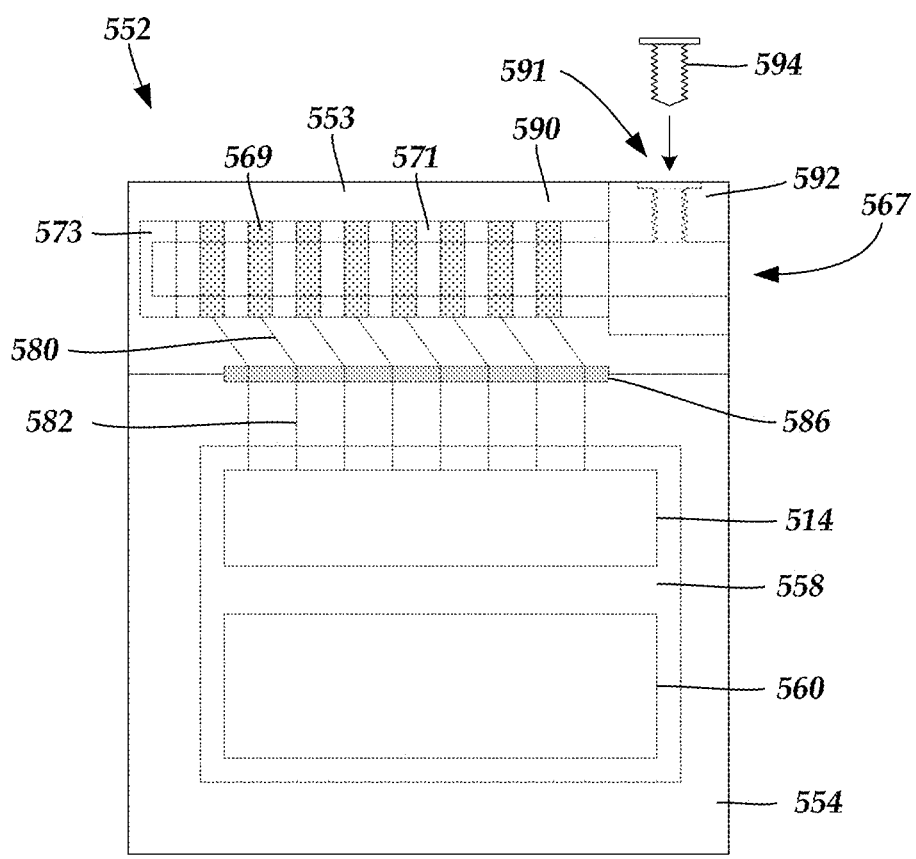
FIG. 5 is a schematic side view of one embodiment of a control module suitable for receiving either the lead of FIG. 2 or the lead extension of FIG. 3.

FIG. 5 shows, in schematic cross-sectional side view, a control module 552 suitable for coupling with an elongated member (e.g., the lead 212, the lead extension 312, or other intermediary device). The control module 552 includes a header 553 disposed along an outer surface of a sealed housing 554 that contains an electronic subassembly 558 with a pulse generator 514 and, optionally, a power supply 560.

A connector assembly 590 is disposed in the header 553. The connector assembly 590 is configured to receive an elongated device (e.g., the lead 212, the lead extension 312, or other intermediary device). The connector assembly 590 defines a connector lumen 567 configured to receive the proximal portion of the elongated member. An array of connector contacts, such as connector contact 569, is arranged along the connector lumen 567 and configured to electrically couple with terminals of the elongated member when the proximal portion of the elongated member is received by the connector 590. The connector contacts can be electrically isolated from one another by electrically-nonconductive spacers, such as spacer 571. The connector stack may also include an end stop 573 to promote alignment of the elongated-member terminals with the connector contacts.

Wires or contacts, such as wire 582, are electrically coupled to the electrical subassembly 558 and extend within the sealed housing 554 to a feedthrough interface 586 disposed along an interface between the header 553 and the sealed housing 554. The connector contacts are electrically coupled to interconnect conductors, such as wire 580, that extend along the header 553 and electrically couple the connector contacts to the wires 582 (and possibly feedthrough pins) at the feedthrough interface 586. In some embodiments, the header 553 is positioned over the feedthrough interface 586.

The connector assembly 590, optionally, includes a retention assembly for facilitating retention of the proximal portion of the elongated member when the proximal portion of the elongated member is received by the control module 552. In the illustrated embodiment, the retention assembly includes a retention block 592. The retention block 592 is positioned to align with a retention sleeve (see e.g., 608 in FIG. 6) of the elongated member when the elongated member is received by the connector assembly 590. In the illustrated embodiment, the retention assembly further includes a retention lumen 591 and a retaining member (e.g., a set screw, a pin, or the like) 594 for insertion into the retention lumen and pressing the retention sleeve of the inserted elongated member against the retention block to retain inserted elongated member within the connector assembly 590.

Figure 6:
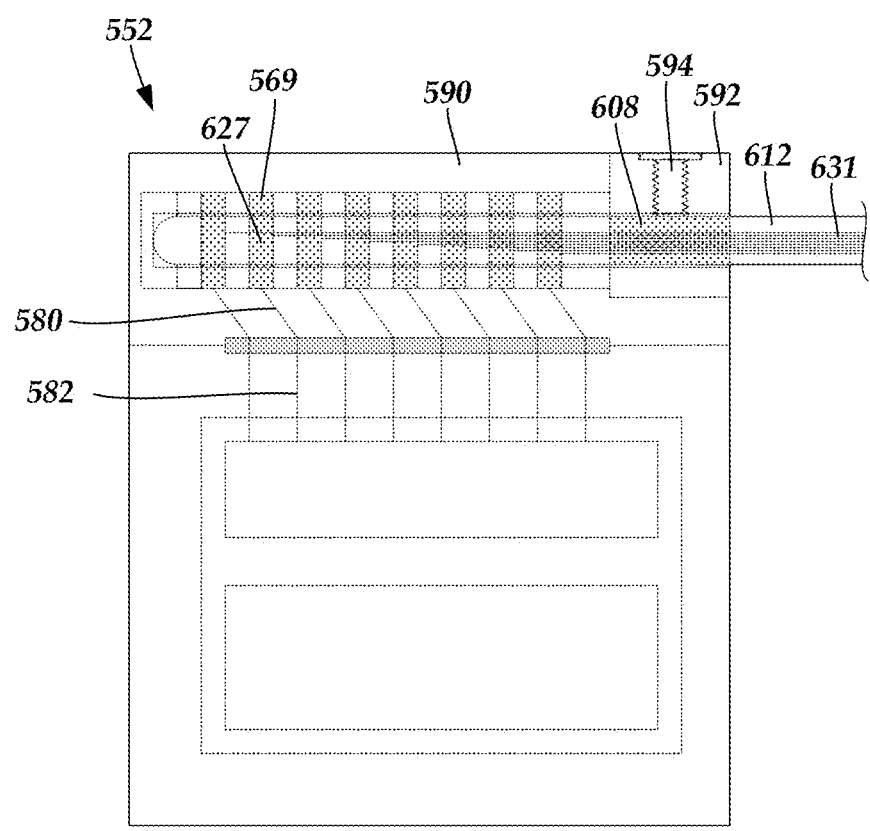
FIG. 6 is a schematic side view of one embodiment of an elongated member retained by the control module of FIG. 5.

FIG. 6 shows, in schematic side view, one embodiment of an elongated member 612 (e.g., the lead 212, the lead extension 312, or other intermediary device) received by the connector assembly 590 of the control module 552. In the illustrated embodiment, the elongated-member terminals, such as elongated-member terminal 627, are aligned with the connector contacts, such as connector contact 569. Accordingly, the elongated-member conductors 631 are electrically coupled with the interconnect conductors 580 and feedthrough interconnects 582. Additionally, in the illustrated embodiment a retention sleeve 608 disposed along the elongated member 612 is aligned with the retention block 592 and the retaining member 594 is pressing the retention sleeve 608 against the retention block 592 to retain the elongated member 612 within the connector assembly 590.

Connector receptacles, such as those in a lead extension or the header of a control module, may be constructed out of materials, such as silicone, that can be susceptible to stretching upon insertion of the proximal end of a lead or lead extension. This may present difficulties in aligning the connector contacts in the connector with the terminals or contacts on the proximal end of the lead or lead extension. In at least some instances, conventional connectors rely on the user (e.g., a physician or clinician) to visually ensure the alignment. Over- or under-insertion may result in misalignment or failure of alignment between the connector contacts in the connector with the terminals or contacts on the proximal end of the lead or lead extension. These circumstances may also increase the time needed for the implantation procedure.

To facilitate correct insertion, arrangements are described herein for providing a tactile indication when the connector is properly aligned with the proximal end of the lead or lead extension being inserted. In at least some embodiments, novel lead or lead extension retention arrangements are also presented. In the illustrated embodiments described below, a lead extension connector, such as lead extension connector 390 of FIGS. 3 and 4, is utilized as an example. It will be understood, however, that the embodiments can also be utilized in control module connectors, such as connector assembly 590 of FIGS. 5 and 6 of a control module, or any other suitable connector. The illustrated embodiments also illustrate a lead, such as lead 212 of FIG. 2, but it will be understood that a lead extension, such as lead extension 312, or any other elongated member with terminals or contacts can be utilized instead.

Figure 7:
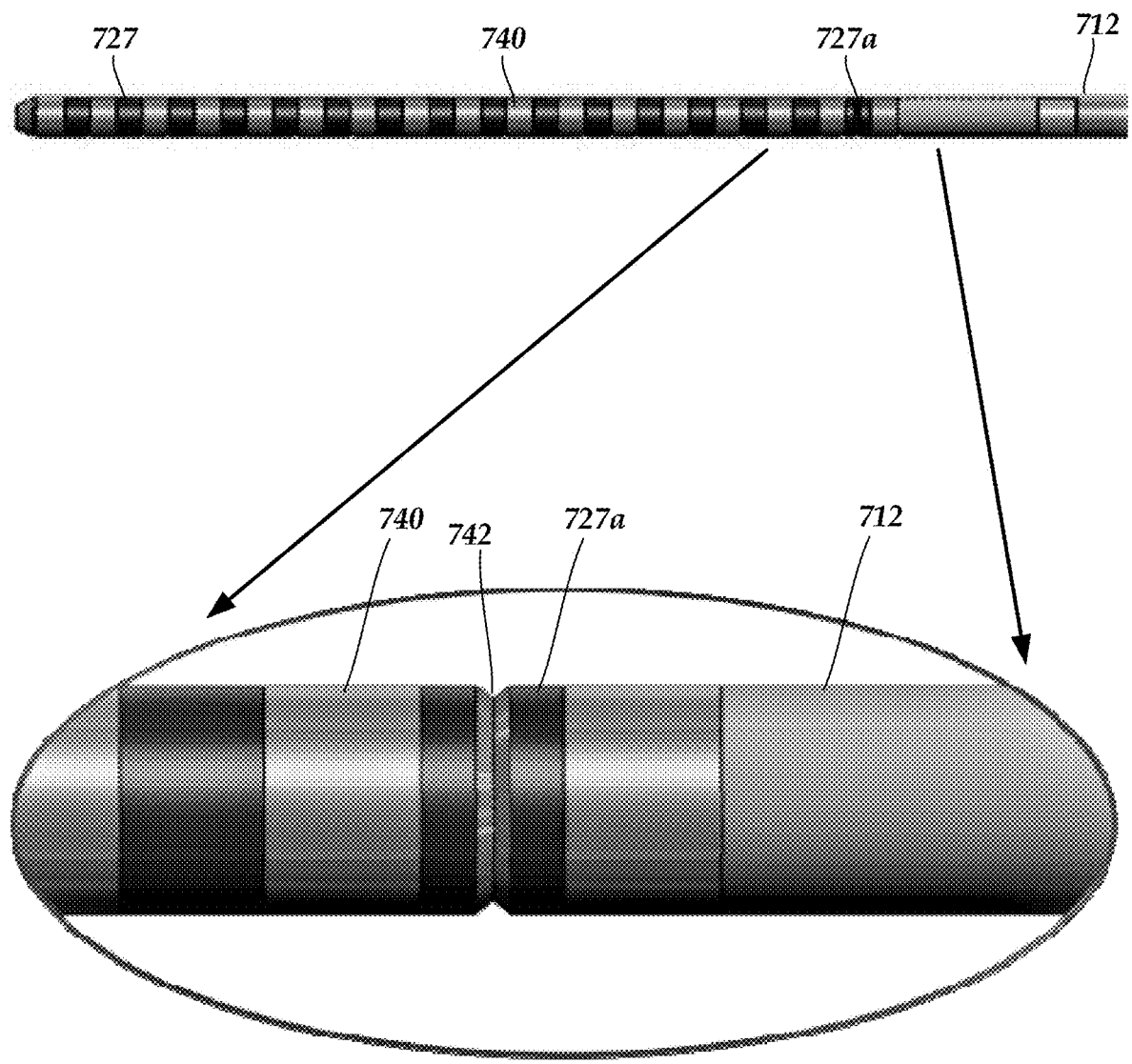
FIG. 7 is a schematic side view of a proximal portion of one embodiment of a lead, including an expanded region, illustrating a terminal with an indented circumferential groove.

FIG. 7 illustrates the proximal end portion of one embodiment of a lead 712 with terminals 727 that are separated by spacers 740. FIG. 7 further illustrates an expanded portion of the lead 712 near the distal-most terminal 727a. To facilitate alignment with a connector, one of the terminals 727a includes an indented circumferential groove 742. In the illustrated embodiments, the distal-most terminal 727a includes the circumferential groove 742. In other embodiments, a different one of the terminals 727 may include a circumferential groove. In some embodiments, more than one of the terminals 727 (for example, 2, 3, 4, 6, 8, or all of the terminals) includes a circumferential groove 742.

In the illustrated embodiments, the circumferential groove 742 extends around the entire circumference of the terminal 727a. In other embodiments, the circumferential groove 742 extends around less than the entire circumference of the terminal 727a, but does extend at least 20%, 25%, 33%, 50%, 66%, or 75% of the circumference of the terminal 727a.

Figure 8A:
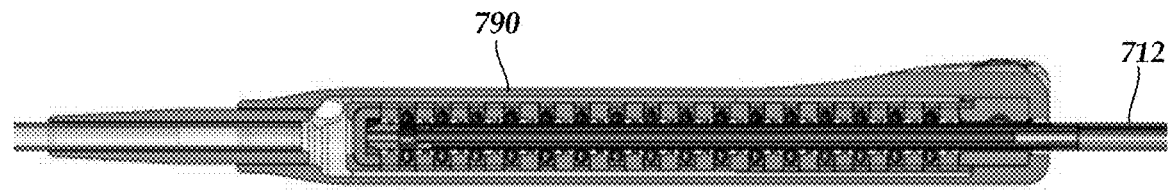
FIG. 8A is a schematic cross-sectional view of one embodiment of a portion of a connector with the proximal portion of the lead of FIG. 7 inserted.
Figure 8B:
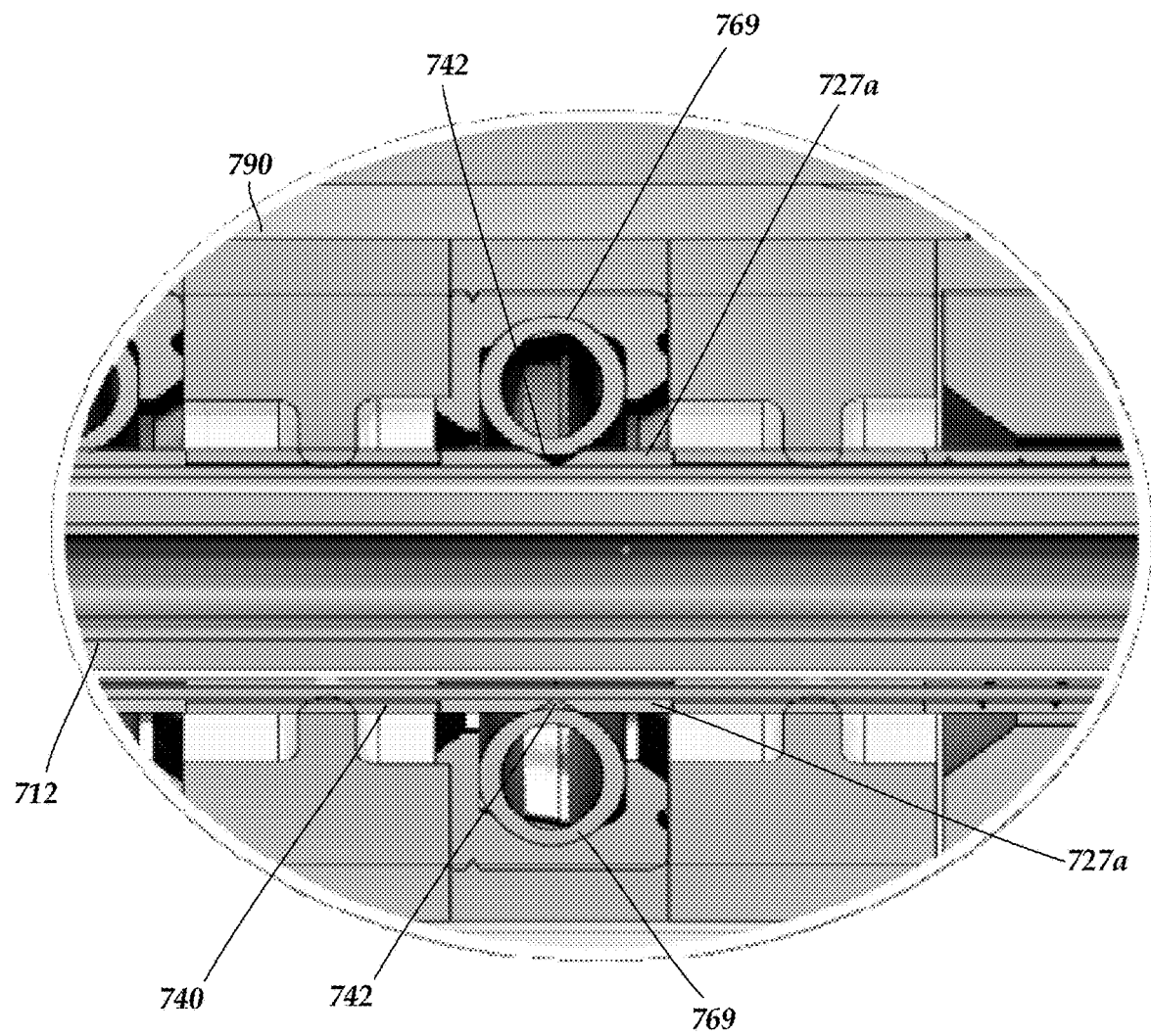
FIG. 8B is an expanded region of the connector and lead of FIG. 8A.

FIG. 8A illustrates the proximal portion of the lead 712 inserted into the lead extension connector 790. FIG. 8B is an expanded portion of the lead 712 and lead extension connector 790 illustrating the terminal 727a with the circumferential groove 742 and a connector contact 769 that is configured to interact with the circumferential groove. In at least in some embodiments, the connector contact 769 may extend partially into, or be seated into, the circumferential groove 742. The interaction between the circumferential groove 742 of the terminal 727a and the connector contact 769 provides a tactile sensation to the user inserting the proximal portion of the lead 712 into the lead extension connector 790 and, through that tactile sensation, indicating that the terminal 727a is aligned with the connector contact 769. In some embodiments, in addition to, or as an alternative to, a tactile sensation, an audible sound (for example, a click) may also be heard as the connector contact 769 interacts with the circumferential groove 742.

Any suitable connector contact 769 can be used including, but not limited to, coiled contacts, canted coil contacts, ball contacts, ring contacts, and the like or any combination thereof. Groove depth, groove width, connector contact width, connector contact placement, and materials of the terminal and connector contact can be selected to provide a desired amount of tactile sensation.

When the circumferential groove 742 is in the distalmost terminal 727a, the tactile sensation indicates to the user that the terminal 727a is aligned with the connector contact 769. In other embodiments, where a circumferential groove is provided in one or more of the other terminals, there may be multiple instances of the tactile sensation as the user inserts the proximal end of the lead or lead extension into the connector. For example, in an eight electrode lead with a circumferential groove in the most proximal terminal, there may be up to eight consecutive tactile sensations as the most proximal terminal is pushed past each of the connector contacts. Providing circumferential grooves in multiple terminals may increase the tactile sensation as multiple conductor contacts interact with the multiple circumferential grooves.

Figure 9A:
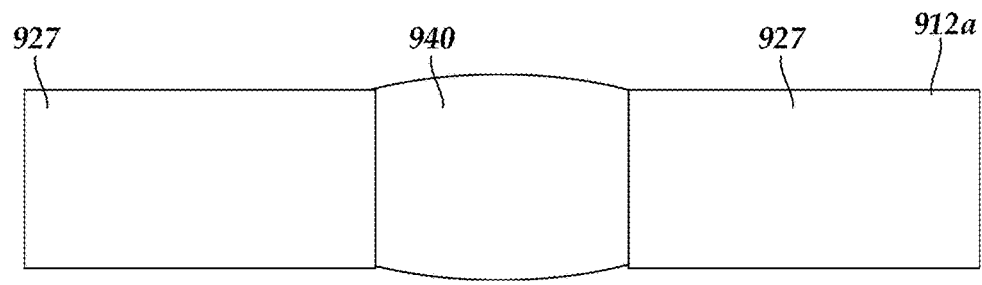
FIG. 9A is a schematic side view of a portion of one embodiment of a lead with a spacer having a larger outer diameter than adjacent terminals.

FIG. 9A illustrates a portion 912a of an embodiment of a lead with terminals 927 and a spacer 940 that has a larger outer diameter than the adjacent terminals. As the spacer 940 pushes past each connector contact (see, for example, connector contact 769) there is a tactile sensation that the user experiences. In at least some embodiments, the outer diameter, at its largest extent, of the spacer 940 is at least 5%, 10%, or more larger than the outer diameter, at its largest extent, of the adjacent terminals 927.

In at least some embodiments, only one spacer 940 has the larger outer diameter with the other spacers having the same diameter as the terminals 927. For example, the spacer 940 adjacent to, and proximal to, the distalmost terminal 927 may have the larger outer diameter so that as it is pushed past the distalmost connector contact of the connector a tactile sensation is experienced by the user.

In other embodiments, multiple spacers 940 (or even all of the spacers 940) have the larger outer diameter. For example, if all of the spacers 940 have the larger outer diameter, a tactile sensation may be experienced as the spacers 940 are pushed past each of the connector contacts.

Figure 9B:
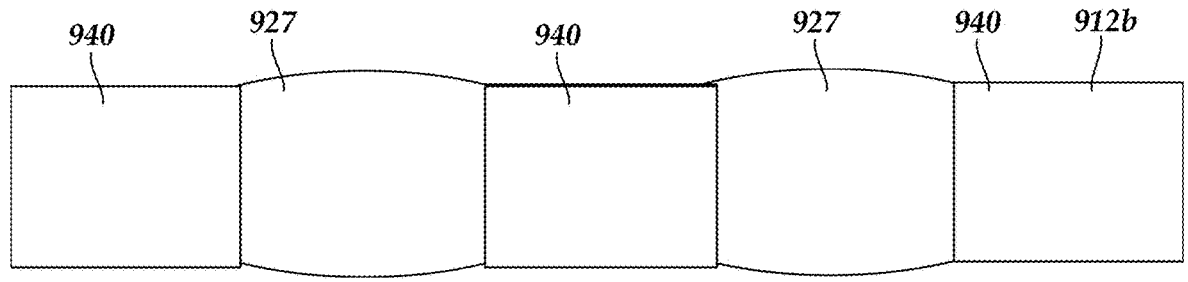
FIG. 9B is a schematic side view of a portion of one embodiment of a lead with terminals having larger outer diameters than adjacent spacers.

FIG. 9B illustrates a portion 912b of another embodiment of a lead with terminals 927 and spacers 940 where one or more of the terminals has a larger outer diameter than the adjacent spacers. As a terminal 927 with a larger diameter pushes past each connector contact (see, for example, connector contact 769) there is a tactile sensation that the user experiences.

In at least some embodiments, the outer diameter, at its largest extent, of the terminal 927 is at least 5%, 10%, or more larger than the outer diameter, at its largest extent, of the adjacent spacers 942.

In at least some embodiments, only one terminal 940 has the larger outer diameter with the other terminals having the same diameter as the terminals 927. For example, the penultimate terminal, with respect to the proximal end of the lead (i.e., the terminal proximal to the distalmost terminal), may have the larger outer diameter so that as it is pushed past the distalmost connector contact of the connector a tactile sensation is experienced by the user.

In other embodiments, multiple terminals 927 (or even all of the terminals 927) have the larger outer diameter. For example, if all of the terminals 927 have the larger outer diameter, a tactile sensation may be experienced as the terminals 927 are pushed past each of the connector contacts.

In some embodiments, in addition to, or as an alternative to, a tactile sensation, an audible sound (for example, a click) may also be heard as spacer(s) 940 or terminal(s) 927 with the larger outer diameters push past the connector contact(s) 769.

Figure 10A:
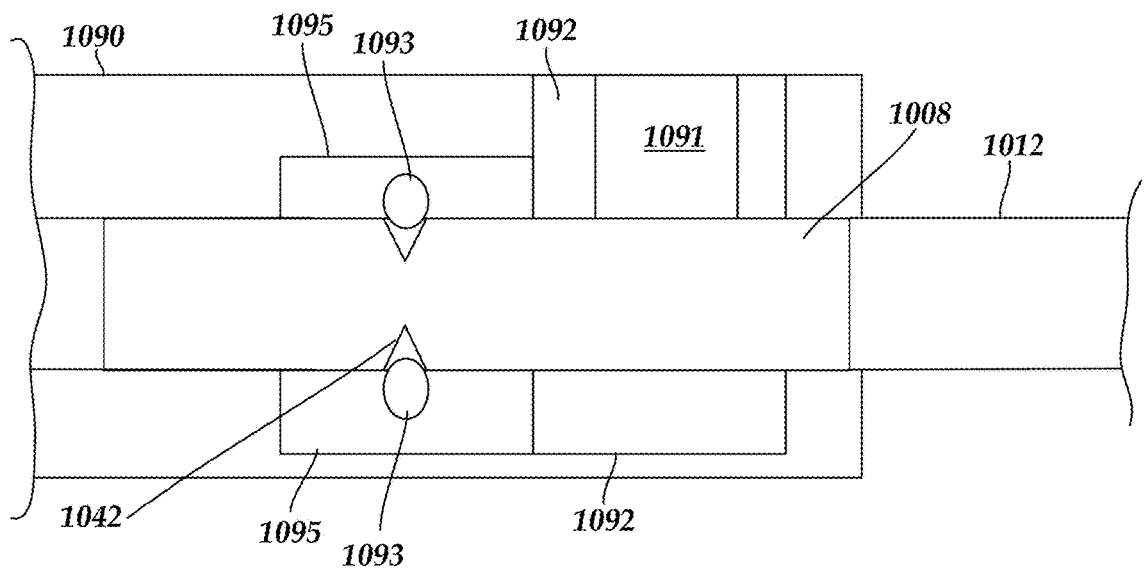
FIG. 10A is a schematic cross-sectional view of one embodiment of a portion of a connector with the proximal portion of a lead inserted illustrating a retention contact interacting with a circumferential groove in a retention sleeve of the lead.

FIG. 10A illustrates an embodiment in which a retention sleeve 1008 is disposed on a lead 1012 and includes a circumferential groove 1042. A connector 1090 (similar to, for example, connector 390 of FIG. 3) includes a retention block 1092 with a retention lumen 1091 for receiving the retaining element (see, retaining element 394 in FIG. 3), a contact housing 1095, and a retention contact 1093 (which may be similar to the connector contact 769 in FIG. 8B). The retention contact 1093 of the retention block is configured to interact with, and, at least in some embodiments, extend partially into, the circumferential groove 1042 of the retention sleeve 1008. In at least some embodiments, the retention contact 1093 may extend partially into, or be seated into, the circumferential groove 1042 of the retention sleeve. The interaction between the circumferential groove 1042 of the retention sleeve 1008 and the retention contact 1093 provides a tactile sensation to the user inserting the proximal portion of the lead 1012 into the lead extension connector 1090 and, through that tactile sensation, indicating that the terminals of the lead 1012 are aligned with the connector contact of the connector 1090. In some embodiments, in addition to, or as an alternative to, a tactile sensation, an audible sound (for example, a click) may also be heard as the retention contact 1093 interacts with the retention sleeve 1008.

Figure 10B:
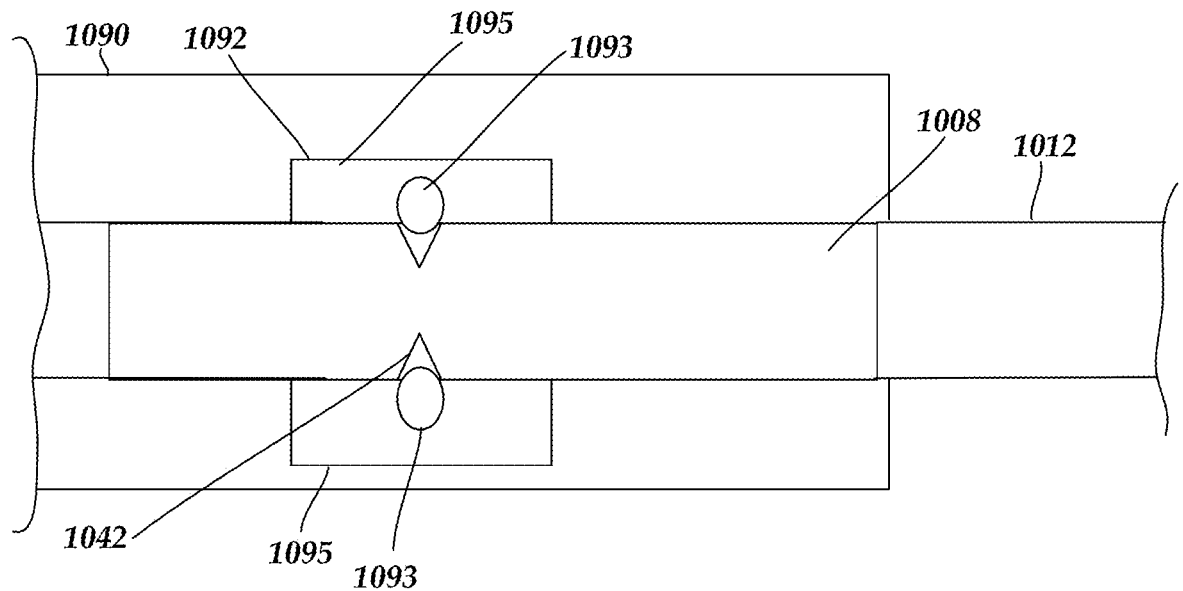
FIG. 10B is a schematic cross-sectional view of another embodiment of a portion of a connector with the proximal portion of a lead inserted illustrating a retention contact interacting with a circumferential groove in a retention sleeve of the lead.

FIG. 10B illustrates another embodiment in which a retention sleeve 1008 is disposed on a lead 1012 and includes a circumferential groove 1042. In this embodiment, however, the connector 1090 has a retention block 1092 that includes a contact housing 1095 and a retention contact 1093 (which may be similar to the connector contact 769 in FIG. 8B), but the retention block 1092 does not include a retention lumen nor is a retaining element used to hold the lead within the connector. Instead, the retention contact 1093 is configured to interact with, and, at least in some embodiments, extend partially into, the circumferential groove 1042 in the retention sleeve 1008 to hold the lead in the connector 1090, as well as provide the tactile sensation to the user as the retention contact 1093 interacts with the circumferential groove 1042. In at least in some embodiments, the retention contact 1093 may extend partially into, or be seated into, the circumferential groove 1042. Groove depth, groove width, retention contact width, retention contact placement, and materials of the retention sleeve, retention contact, and retention block can be selected to provide a desired amount of retention and tactile sensation.

Figure 10C:
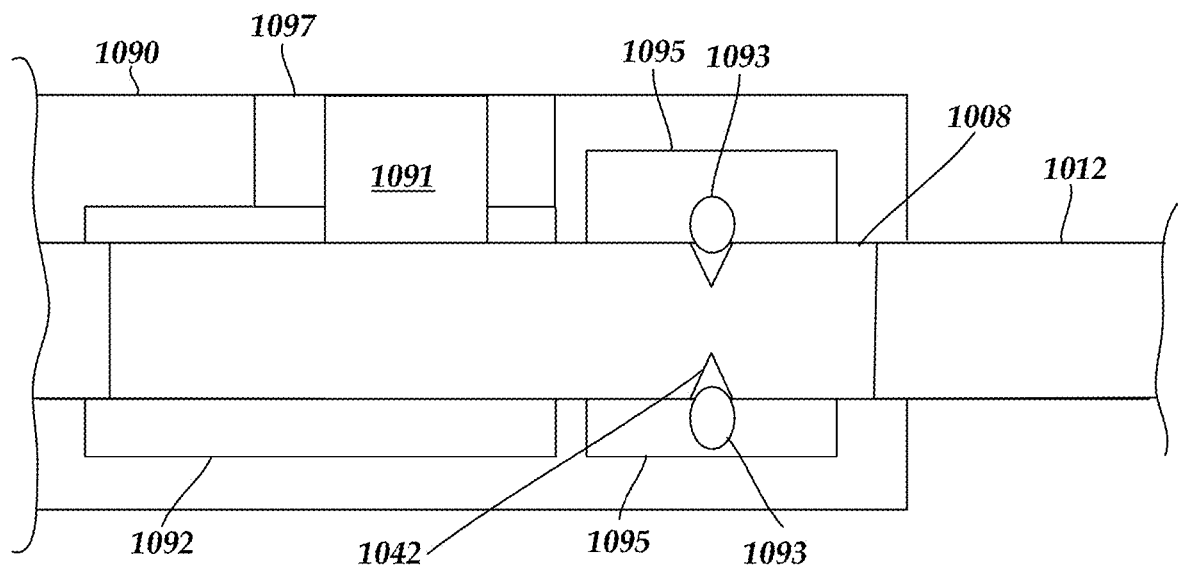
FIG. 10C is a schematic cross-sectional view of a third embodiment of a portion of a connector with the proximal portion of a lead inserted illustrating a retention contact interacting with a circumferential groove in a retention sleeve of the lead.

FIG. 10C illustrates yet another embodiment in which a retention sleeve 1008 is disposed on a lead 1012 and includes a circumferential groove 1042. A connector 1090 includes a retention block 1092 with a retention lumen 1091 for receiving a retaining element (see, for example, retaining element 394 of FIG. 3), a contact housing 1095, and a retention contact 1093 (which may be similar to the connector contact 769 in FIG. 8B) that is configured to interact with, and, at least in some embodiments, extend partially into, the circumferential groove. In at least in some embodiments, the retention contact 1093 may extend partially into, or be seated into, the circumferential groove 1042. In the illustrated embodiment of FIG. 10C, the contact housing 1095 and retention contact 1093 are distal to the remainder 1097 of the retention block 1092. In at least some embodiments, the contact housing 1095 may be physically separated from the remainder 1097 of the retention block and still reside in the connector 1090. In other embodiments, the contact housing 1095 and retention contact 1093 may be attached to the connector 1090 or other disposed external to the connector 1090. For example, the contact housing 1095 and retention contact 1093 may be adhesively attached to the connector 1090 in order to retrofit an existing connector and provide an arrangement for producing the tactile sensation when the lead, lead extension, or other elongated element is inserted into the connector.

In the illustrated embodiments of FIGS. 10A-10C, the circumferential groove 1042 extends around the entire circumference of the retention sleeve 1008. In other embodiments, the circumferential groove 1042 extends around less than the entire circumference of the retention sleeve, but does extend at least 10%, 20%, 25%, 33%, 50%, 66%, or 75% of the circumference of the retention sleeve 1008.

In the illustrated embodiments of FIGS. 10A-10C, the retention contact 1093 can be a coil or other contact which allows the lead to be inserted into the connector 390 and past the retention contact 1093 and also allows the lead to be retracted from the connector 390 by pulling on the lead. In other embodiments, the retention contact 1093 can be a contact, such as a spring-loaded pogo pin, that permits the lead to be inserted into the connector 390 and past the retention contact 1093, but, upon engagement of the retention contact 1093 with the circumferential groove 1042, does not allow the retraction of the lead from the connector 1090. Such an arrangement can prevent inadvertent dislodgement of the lead from the connector. In at least some of these embodiments, the retention block 1092 or contact housing 1095 can include a port for access by a tool to retract the retention contact 1093 from engagement with the circumferential groove 1042 of the lead 1012 to permit retraction of the lead from the connector 390.

It will be understood that any combination of the elements illustrated in FIGS. 7 to 10C can be used. For example, any combination of a circumferential groove in one or more terminals, a circumferential groove in a retention sleeve, and spacer(s)/terminal(s) with larger outer diameters than adjacent terminal(s)/spacer(s) can be used on a lead, lead extension, or other elongated body. In addition, any of the retention blocks 1092 illustrated in FIGS. 10A to 10C can be used with any of the leads, lead extensions, or other elongated bodies disclosed herein.

Figure 11:
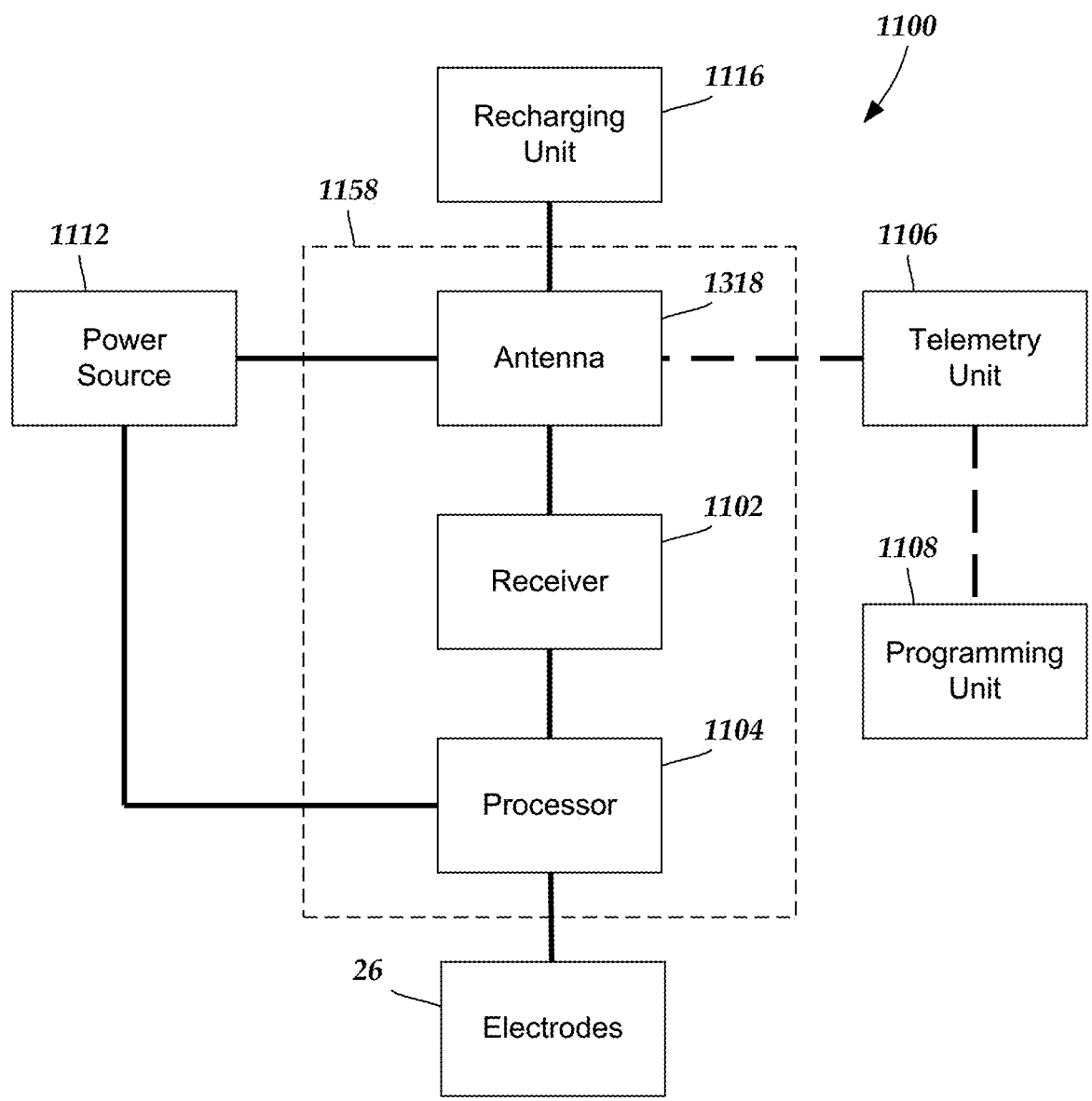
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1158 disposed within a control module. The electronic subassembly 1158 may include one or more components of the IPG. It will be understood that the electrical stimulation system can include more, fewer, or different components and can have a variety of different configurations including those configurations disclosed in the stimulator references cited herein.

Some of the components (for example, a power source 1112, an antenna 1118, a receiver 1102, and a processor 1104) of the electrical stimulation system can be positioned on one or more circuit boards or similar carriers within a sealed housing of an implantable pulse generator (see e.g., 14 in FIG. 1), if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1118 or a secondary antenna. In at least some embodiments, the antenna 1118 (or the secondary antenna) is implemented using the auxiliary electrically-conductive conductor. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above. The electronic subassembly 1158 and, optionally, the power source 1112 can be disposed within a control module (e.g., the IPG 14 or the ETS 20 of FIG. 1).

In one embodiment, electrical stimulation signals are emitted by the electrodes 26 to stimulate nerve fibers, muscle fibers, or other body tissues near the electrical stimulation system. The processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 selects which electrode(s) are cathodes and which electrode(s) are anodes. In some embodiments, the processor 1104 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by the programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and the receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include the antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification and examples provide a description of the manufacture and use of the invention. Since many embodiments of the invention can be made without departing from the spirit and scope of the invention, the invention also resides in the claims hereinafter appended.

The invention claimed is:

1. A stimulation system, comprising:
   a connector defining a connector port and a connector lumen extending from the connector port, the connector comprising a plurality of connector contacts disposed along the connector lumen; and
   an implantable lead comprising
      a lead body having a proximal end section and a distal end section,
      a plurality of electrodes arranged along the distal end section of the lead body,
      a plurality of terminals arranged along the proximal end section of the lead body,
   wherein the terminals and the electrodes are conductive and at least one of the terminals comprises an indented circumferential groove around an exterior of the at least one of the terminals, and
      a plurality of conductors extending within the lead body and electrically coupling the electrodes to the terminals;
   wherein the connector lumen is configured for user insertion of the proximal end section of the lead body of the implantable lead and, when fully inserted, align the connector contacts of the connector with the terminals of the implantable lead, wherein the connector and the implantable lead are configured so that alignment of the at least one of the terminals with the indented circumferential groove with at least one of the connector contacts produces a tactile sensation for the user inserting the proximal end section of the lead body into the connector lumen.

2. The stimulation system of claim 1, wherein a distalmost terminal of the plurality of terminals comprises the indented circumferential groove.

3. The stimulation system of claim 1, wherein a plurality of the terminals each comprises the indented circumferential groove.

4. The stimulation system of claim 1, wherein the indented circumferential groove extends around an entire circumference of the at least one of the terminals.

5. The stimulation system of claim 1, wherein the indented circumferential groove does not extend around an entire circumference of the at least one of the terminals, but does extend around at least 20% of the circumference of the at least one of the terminals.

6. The stimulation system of claim 1, wherein the connector and the implantable lead are configured so that alignment of the at least one of the terminals with the indented circumferential groove with at least one of the connector contacts produces a sound audible to the user inserting the proximal end section of the lead body into the connector lumen as the indented circumferential groove interacts with the at least one of the connector contacts.

7. The stimulation system of claim 1, wherein the implantable lead further comprises a retention sleeve disposed along the proximal end section of the lead body and distal to the terminals and the connector further comprises a retention block.

8. The stimulation system of claim 7, wherein the retention block further defines a retention lumen for receiving a retaining element for pressing against the retention sleeve of the lead for retention of the implantable lead within the connector.

9. The stimulation system of claim 7, wherein the retention block does not include a retention lumen and the retention block is configured for exerting a force against the retention sleeve to retain the implantable lead within the connector.

10. The stimulation system of claim 7, wherein the retention block is adhesively attached to a remainder of the connector.

11. The stimulation system of claim 7, wherein the retention sleeve comprises an indented circumferential retention groove.

12. The stimulation system of claim 11, wherein the retention block comprises a retention contact disposed along the connector lumen or distal to the connector lumen.

13. The stimulation system of claim 12, wherein the connector and implantable lead are configured so that alignment of the indented circumferential retention groove of the retention sleeve with the retention contact produces a tactile sensation for the user inserting the proximal end section of the lead body into the connector lumen.

14. The stimulation system of claim 11, wherein the indented circumferential retention groove extends around an entire circumference of the retention sleeve.

15. The stimulation system of claim 11, wherein the indented circumferential retention groove does not extend around an entire circumference of the retention sleeve, but does extend around at least 20% of the circumference of the retention sleeve.

16. The stimulation system of claim 1, further comprising a control module, wherein the connector is part of the control module.

17. The stimulation system of claim 1, further comprising a lead extension, wherein the connector is part of the lead extension.

18. The stimulation system of claim 1, wherein the implantable lead comprises a plurality of spacers with each of the spacers separating adjacent ones of the terminals.

19. The stimulation system of claim 18, wherein at least one of the spacers has a larger outer diameter than an outer diameter of the terminals.

* * * * *